United States Patent [19]

Pannwitz

[11] Patent Number: 4,692,309
[45] Date of Patent: Sep. 8, 1987

[54] DIFFUSION SAMPLE COLLECTOR FOR GASEOUS MEDIA

[75] Inventor: Karl-Heinz Pannwitz, Lübeck, Fed. Rep. of Germany

[73] Assignee: Dragerwerk AG, Fed. Rep. of Germany

[21] Appl. No.: 904,888

[22] Filed: Sep. 8, 1986

[30] Foreign Application Priority Data

Sep. 5, 1985 [DE] Fed. Rep. of Germany ....... 3531650

[51] Int. Cl.⁴ .............................................. G01J 1/48
[52] U.S. Cl. ........................................ 422/87; 422/88
[58] Field of Search ................ 73/863, 863.21, 863.23, 73/864, 864.51, 864.91, 23; 422/83, 86, 87, 88, 94

[56] References Cited

U.S. PATENT DOCUMENTS

| 1,321,062 | 11/1919 | Lamb et al. | 422/88 |
| 2,097,650 | 11/1937 | Stampe | 422/88 |
| 3,022,141 | 2/1962 | Grosskopf | 422/86 |
| 3,033,655 | 5/1962 | Grosskopf | 422/88 |
| 3,113,842 | 12/1963 | Udall | 422/86 |
| 3,884,641 | 5/1975 | Kraffczyk et al. | 422/87 |
| 4,267,023 | 5/1981 | Frant et al. | 422/83 |
| 4,300,910 | 11/1981 | Pannwitz | 422/88 |
| 4,348,358 | 9/1982 | McKee et al. | 422/87 |
| 4,350,037 | 9/1982 | Higham | 422/88 |
| 4,481,297 | 11/1984 | Zucal et al. | 422/88 |
| 4,554,133 | 11/1985 | Leichnitz | 422/87 |

FOREIGN PATENT DOCUMENTS 0039380 3/1979 Japan ..................................... 422/88

Primary Examiner—Stewart J. Levy
Assistant Examiner—Robert R. Raevis
Attorney, Agent, or Firm—McGlew and Tuttle

[57] ABSTRACT

A diffusion sample collector for gaseous media, consisting of a transparent container open at both ends, which contains a collecting layer and has at its two open ends permeable retaining elements. The collector is improved in such a manner that the presence of hazardous substances in the surrounding air to be analyzed can be recognized during the collecting of the samples in order that an unnecessary analysis of the collecting layer can be prevented in the absence of hazardous substances and also gas eruptions can be noticed immediately. For this latter purpose, an additional layer is provided in the container, which is separated from the collecting layer by a dividing wall and is in contact with the gas to be analyzed through the opposite end and its retaining element.

6 Claims, 2 Drawing Figures 4,692,309

DIFFUSION SAMPLE COLLECTOR FOR GASEOUS MEDIA

FIELD AND BACKGROUND OF THE INVENTION

The invention concerns a diffusion sample collector for gaseous media, comprising a transparent container open at both ends, which contains a collecting layer and has permeable retaining elements at its two open ends.

A diffusion sample collector of this type was known from German OS No. 30 12 380.

The known sample collector consists of a transparent tube that is filled with a collecting layer, for example activated charcoal, and is closed at its two ends with a porous diffusion grid. Such sample collectors are carried by persons working in an environment where the air contains hazardous components. The hazardous substances collected during the stay in the hazardous air are determined by a subsequent laboratory analysis of the collecting layers. For this purpose, the hazardous substance adsorbed by the collecting layer is chemically dissolved and determined. The amount of determined hazardous substance indicates, with respect to the carrying time, the average exposure of the person.

A considerable disadvantage of this known sample collector is the fact that prior to a laboratory analysis, it is impossible to see whether an exposure to hazardous substances did in fact occur. This finding is obtained only from the complicated laboratory analysis, which is subsequently proven to be unnecessary if no exposure occurred. Besides, the known sample collector allows only a conclusion to be drawn with respect to the amount of a hazardous substance accumulated within a unit of time. When the amount of hazardous substances increases rapidly during the time of exposure, this fact is not indicated by the sample collector and the person in question does not receive any warning of possible danger from which he might escape through eventual flight.

SUMMARY OF THE INVENTION

The present invention proceeds from the task of improving the diffusion sample collector of the known type in such a manner that even during the sample collecting the presence of hazardous substances in the surrounding air to be analyzed can be recognized in order that an unnecessary laboratory analysis of the collecting layer is avoided in the absence of hazardous substances and, also, the persons affected can take proper steps for their protection during gas eruptions.

This task is solved by providing in the container an additional indicator layer, which is separated from the collecting layer by a dividing wall and is in contact with the gas to be analyzed through the retaining elements.

The main advantage of the invention is the fact that the indicator layer can be used to establish whether an exposure has occurred and whether a subsequent laboratory analysis of the collecting layer is necessary. The carrier of the sample collector can judge himself by observation of the indicator whether he is moving in an atmosphere loaded with hazardous substance. In the event of an unusually fast rise in the indicator reading, the person in question is informed early of a possible danger, permitting him to start proper counter-measures. An additional advantage is seen in the fact that a sample collector that obviously was not exposed to any hazardous substance can be continued to be used without any detriment. This increases the life of the sample collector.

The indicator layer preferably comprises an impregnated, granular substrate that discolors in the presence of the gas component to be collected. Substrate and impregnation are adjusted for the detection of the hazardous substance components, as is known from the area of the testing tubes. For example, the granular substrate comprises glass grit, impregnated with chromium sesqui-oxide and a mixture of dilute phosphoric acid and sulfuric acid, if alcohol vapors are to be detected. For the indication of aromatic hydrocarbons such as benzene or toluene, silica gel is used as granular substrate, which is impregnated with paraformaldehyde and concentrated sulfuric acid.

In a different practical example of the invention, an impregnated paper strip can be used instead of a granular indicator layer. This provides a greater indicator accuracy for the zone of discoloration.

When gaseous substances are to be detected that do not cause any immediate discoloration in the indicator layer, a porous reagent layer for the conversion of the gas component to be detected into substances that discolor the indicator layer is inserted between the impermeable dividing wall and the indicator layer. Such a reagent layer is particularly useful when chlorinated hydrocarbons such as vinyl chloride are to be detected. For this purpose, the reagent layer comprises preferably granular aluminum silicate, which is impregnated with chromium sequi-oxide and sulfuric acid. Chlorine is released as reaction product in the reagent layer, which is subsequently determined by a color reaction in the indicator layer consisting, for example, of silica gel impregnated with o-tolidine.

Impregnations of the indicator layer that are affected by water vapor are protected to advantage by attaching a drying layer in front of the indicator layer.

Accordingly it is an object of the present invention to provide a diffuser sample collector for gaseous media which comprises a transparent container which has an opening at each end and which includes a non-permeable wall between the ends dividing the container into two compartments one of which is filled with a collecting layer of material and the other of which is filled with an indicating layer of material.

A further object of the invention is to provide a device for readily collecting a gaseous sample and for also indicating the presence of gases immediately.

A further object of the invention is to provide a diffuser sample collector which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
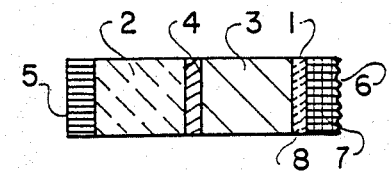
FIG. 1 is a section through a diffusion sample collector constructed in accordance with the invention.

Referring to the drawings in particular, the invention as embodied therein in FIG. 1 includes a diffusion sample collector for gaseous media which comprises a transparent container 1 having an opening at each end and with a non-permeable wall 4 in the container dividing it into two compartments, one of which is filled with a collecting layer of material 2, and the other of which is filled with an indicating layer of material 3.

In FIG. 1, container 1 of the sample collector is filled to one-half with a collecting layer 2, e.g. activated charcoal, and with an impregnated, granular substrate as an indicator layer 3. The activated charcoal 2 and the indicator layer 3 are separated from each other by a dividing wall 4. Both ends of the container 1, which may be a glass tube, for example, are closed with permeable retaining elements 5, 6. While the one retaining element 5 for the activated charcoal 2 may consist of acetate cellulose, the second retaining element providing a drying layer 7 is inserted in front of (interiorly of) the indicator layer 6 and comprises a screen cloth, for example.

In the shown condition, the sample collector is exposed to the gas to be analyzed in the open position, when the hazardous substance to be collected is collected in the activated charcoal 2 and a discoloration of the impregnation occurs simultaneously in indicator layer 3, which progresses as a discoloration zone through a reagent layer 8, starting from drying layer 7, during continued exposure time in the direction toward dividing wall 4.

After the exposure, the sample collector can be closed at its ends with two closing caps that are not shown, to prevent rediffusion or subsequent diffusion of additional substances, which could vitiate or spoil the analytical result.

Figure 2:
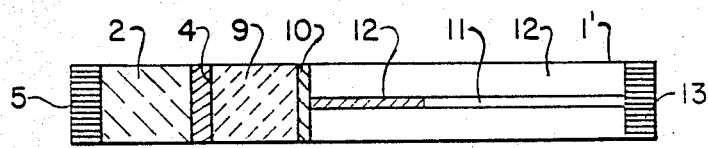
FIG. 2 is a section through another embodiment of the invention showing a diffusion sample collector with a reagent layer and a paper strip as indicator layer.

In FIG. 2, a glass tube 1' is filled with activated charcoal 2 at its one end, which is separated from reagent layer 9 located next to it by the impermeable dividing wall 4. A permeable retaining element 10 follows reagent layer 9 and closes off a partial space 12 of glass tube 1', which contains the indicator layer built up on a paper strip 11. The paper strip 11 with the indicator layer has a discoloration zone 12 on its side facing retaining element 10. Both ends of glass tube 1 are closed with the permeable retaining elements 5,13.

The sample collector shown in FIG. 2 is exposed to an atmosphere containing a hazardous substance that does not discolor paper strip 11 that forms the indicator layer, but must first be broken down into substances by reagent layer 9 that causes a discoloration zone 12 to develop on the indictor layer. This discoloration zone 12 spreads, with continued exposure, from retaining element 10 in the direction toward retaining element 13. After use, this sample collector may also be closed at its ends with two closing caps that are not shown.

While specific embodiments of the invention have been shown and described in detail to illustrate the application of the principles of the invention, it will be understood that the invention may be embodied otherwise without departing from such principles.

What is claimed is:

1. Diffusion sample collector and indicator arrangement for gas components in gaseous media, comprising in combination
    a transparent container having an opening at both ends,
    a non-permeable wall between the ends and dividing the container into two separate compartments, each compartment communicating with a separate open end,
    an indicator layer of material in one of the compartments for indicating the effect of a gas component to which the indicator layer is exposed, and
    a collector layer of material in the other of the compartments for collecting a gas component whose quantity is to be later determined upon the presence of such gas component being indicated by the indicator layer in the one of the compartments.

2. Arrangements of claim 1 wherein the indicator layer comprises an impregnated granulated substrate that is discolored by the effect of the gas component to which such substrate is exposed.

3. Arrangement of claim 1, wherein the indicator layer comprises an impregnated paper strip.

4. Arrangement of claim 1 wherein the wall dividing the container is impermeable and the indicator layer includes a porous reagent layer provided for the conversion of a gas component to be detected into a substance that discolors the indicator layer.

5. Arrangement of claim 1 wherein a drying layer is provided which is located between the open end of the one compartment and the indictor layer in such one compartment.

6. Arrangement of claim 1 wherein a retaining element of porous material is provided at each open end of the container.

* * * * *